(12) United States Patent
Endou et al.

(10) Patent No.: US 6,986,997 B1
(45) Date of Patent: Jan. 17, 2006

(54) METHOD FOR SCREENING USING AN OAT1 TRANSPORTER PROTEIN

(75) Inventors: Hitoshi Endou, 23-7, Yoshinodai 1-chome, Sagamihara-shi, Kanagawa 229-0022 (JP); Yoshikatsu Kanai, Hachioji (JP); Takashi Sekine, Tachikawa (JP); Makoto Hosoyamada, Mitaka (JP)

(73) Assignees: Fuji Bio Medix Co., Ltd., Saitama-Ken (JP); Hitoshi Endou, Kanagawa (JP)

( * ) Notice: Subject to any disclaimer, the term of this patent is extended or adjusted under 35 U.S.C. 154(b) by 0 days.

(21) Appl. No.: 09/424,347

(22) PCT Filed: May 18, 1998

(86) PCT No.: PCT/JP98/02171

§ 371 (c)(1),
(2), (4) Date: Jul. 18, 2000

(87) PCT Pub. No.: WO98/53064

PCT Pub. Date: Nov. 26, 1998

(30) Foreign Application Priority Data

May 23, 1997 (JP) .................................. 9-134182

(51) Int. Cl.
C01N 33/566 (2006.01)
C12N 15/00 (2006.01)
C12N 15/63 (2006.01)
C12N 15/12 (2006.01)

(52) U.S. Cl. .................... 435/7.2; 435/320.1; 435/325; 435/69.1

(58) Field of Classification Search ................ 435/7.2, 435/320.1, 325, 69.1
See application file for complete search history.

(56) References Cited

OTHER PUBLICATIONS

Sekine T, et al. Expression cloning and characterization of a novel multispecific organic anion tranpsorter. J Biol Chem. Jul. 25, 1997;272(30):18526-9.*
Sweet DH, et al. Expression cloning and characterization of ROAT1. The basolateral organic anion tranpsorter in rat kidney. J Biol Chem. Nov. 28, 1997;272(48):30088-95.*
Kanai N et al. Transient expression of oatp organic anion transporter in mammalian cells: identification of candidate substrates Am J Physiol Feb. 1996;270(2 Pt 2):F319-25.*
Mickle JE et al. Genotype-phenotype relationships in cystic fibrosis. Med Clin North Am. May 2000;84(3):597-607.*
Voet et al. Biochemistry. 1990. John Wiley & Sons, Inc. pp. 126-128 and 228-234.*
Yan et al., Two-amino acid molecular switch in an epithelial morphogen that regulates binding to two distinct receptors. Science 290: 523-527, 2000.*

* cited by examiner

Primary Examiner—Joseph Murphy
(74) Attorney, Agent, or Firm—Peter F. Corless; John B. Alexander; Edwards & Angell, LLP

(57) ABSTRACT

A protein capable of transporting organic anions having amino acid sequences represented by SEQ ID NO: 1 or 2 or amino acid sequences derived therefrom by deletion, substitution or addition of one or more amino acid residues; and a gene coding for the protein. The protein and gene therefore are useful in vitro analysis of drug release and drug—drug interactions and development of method for screening drugs useful for preventing nephrotoxicity.

7 Claims, 7 Drawing Sheets

SEQUENCE LISTING

```
<160> NUMBER OF SEQ ID NOS: 4

<210> SEQ ID NO 1
<211> LENGTH: 2171
<212> TYPE: DNA
<213> ORGANISM: Rat
<220> FEATURE:
<221> NAME/KEY: CDS
<222> LOCATION: (268)...(1956)

<400> SEQUENCE: 1
gaaagctgag ctgccctgac ccccaaagtg aggagaagct gcaagggaaa agggagggac      60
agatcaggga gaccggggaa gaaggaggag cagccaagga ggctgctgtc cccccacaga     120
gcagctcgga ctcagctccc ggagcaaccc agctgcggag gcaacggcag tgctgctcct     180
ccagcgaagg acagcaggca ggcagacaga cagaggtcct gggactggaa ggcctcagcc     240
cccagccact gggctgggcc tggccca atg gcc ttt aat gac ctc ctg cag cag     294
                                Met Ala Phe Asn Asp Leu Leu Gln Gln
                                  1               5 gtg ggg ggt gtc ggc cgc ttc cag cag atc cag gtc acc ctg gtg gtc     342
Val Gly Gly Val Gly Arg Phe Gln Gln Ile Gln Val Thr Leu Val Val
 10              15                  20                  25 ctc ccc ctg ctc ctg atg gct tct cac aac acc ctg cag aac ttc act     390
Leu Pro Leu Leu Leu Met Ala Ser His Asn Thr Leu Gln Asn Phe Thr
             30                  35                  40 gct gcc atc cct acc cac cac tgc cgc ccg cct gcc gat gcc aac ctc     438
Ala Ala Ile Pro Thr His His Cys Arg Pro Pro Ala Asp Ala Asn Leu
         45                  50                  55 agc aag aac ggg ggg ctg gag gtc tgg ctg ccc cgg gac agg cag ggg     486
Ser Lys Asn Gly Gly Leu Glu Val Trp Leu Pro Arg Asp Arg Gln Gly
     60                  65                  70 cag cct gag tcc tgc ctc cgc ttc acc tcc ccg cag tgg gga ctg ccc     534
Gln Pro Glu Ser Cys Leu Arg Phe Thr Ser Pro Gln Trp Gly Leu Pro
 75                  80                  85
```

-continued

| | | |
|---|---|---|
| ttt ctc aat ggc aca gaa gcc aat ggc aca ggg gcc aca gag ccc tgc<br>Phe Leu Asn Gly Thr Glu Ala Asn Gly Thr Gly Ala Thr Glu Pro Cys<br>90                             95                           100                            105 | 582 |
| acc gat ggc tgg atc tat gac aac agc acc ttc cca tct acc atc gtg<br>Thr Asp Gly Trp Ile Tyr Asp Asn Ser Thr Phe Pro Ser Thr Ile Val<br>                         110                         115                         120 | 630 |
| act gag tgg gac ctt gtg tgc tct cac agg gcc cta cgc cag ctg gcc<br>Thr Glu Trp Asp Leu Val Cys Ser His Arg Ala Leu Arg Gln Leu Ala<br>              125                         130                         135 | 678 |
| cag tcc ttg tac atg gtg ggg gtg ctg ctc gga gcc atg gtg ttc ggc<br>Gln Ser Leu Tyr Met Val Gly Val Leu Leu Gly Ala Met Val Phe Gly<br>         140                         145                         150 | 726 |
| tac ctt gca gac agg cta ggc cgc cgg aag gta ctc atc ttg aac tac<br>Tyr Leu Ala Asp Arg Leu Gly Arg Arg Lys Val Leu Ile Leu Asn Tyr<br>155                             160                         165 | 774 |
| ctg cag aca gct gtg tca ggg acc tgc gca gcc ttc gca ccc aac ttc<br>Leu Gln Thr Ala Val Ser Gly Thr Cys Ala Ala Phe Ala Pro Asn Phe<br>170                             175                         180                         185 | 822 |
| ccc atc tac tgc gcc ttc cgg ctc ctc tcg ggc atg gct ctg gct ggc<br>Pro Ile Tyr Cys Ala Phe Arg Leu Leu Ser Gly Met Ala Leu Ala Gly<br>                         190                         195                         200 | 870 |
| atc tcc ctc aac tgc atg aca ctg aat gtg gag tgg atg ccc att cac<br>Ile Ser Leu Asn Cys Met Thr Leu Asn Val Glu Trp Met Pro Ile His<br>         205                         210                         215 | 918 |
| aca cgg gcc tgc gtg ggc acc ttg att ggc tat gtc tac agc ctg ggc<br>Thr Arg Ala Cys Val Gly Thr Leu Ile Gly Tyr Val Tyr Ser Leu Gly<br>         220                         225                         230 | 966 |
| cag ttc ctc ctg gct ggt gtg gcc tac gct gtg ccc cac tgg cgc cac<br>Gln Phe Leu Leu Ala Gly Val Ala Tyr Ala Val Pro His Trp Arg His<br>         235                         240                         245 | 1014 |
| ctg cag cta ctg gtc tct gcg cct ttt ttt gcc ttc ttc atc tac tcc<br>Leu Gln Leu Leu Val Ser Ala Pro Phe Phe Ala Phe Phe Ile Tyr Ser<br>250                             255                         260                         265 | 1062 |
| tgg ttc ttc att gag tcg gcc cgc tgg cac tcc tcc tcc ggg agg ctg<br>Trp Phe Phe Ile Glu Ser Ala Arg Trp His Ser Ser Ser Gly Arg Leu<br>                         270                         275                         280 | 1110 |
| gac ctc acc ctg agg gcc ctg cag aga gtc gcc cgg atc aat ggg aag<br>Asp Leu Thr Leu Arg Ala Leu Gln Arg Val Ala Arg Ile Asn Gly Lys<br>         285                         290                         295 | 1158 |
| cgg gaa gaa gga gcc aaa ttg agt atg gag gta ctc cgg gcc agt ctg<br>Arg Glu Glu Gly Ala Lys Leu Ser Met Glu Val Leu Arg Ala Ser Leu<br>                   300                         305                         310 | 1206 |
| cag aag gag ctg acc atg ggc aaa ggc cag gca tcg gcc atg gag ctg<br>Gln Lys Glu Leu Thr Met Gly Lys Gly Gln Ala Ser Ala Met Glu Leu<br>315                             320                         325 | 1254 |
| ctg cgc tgc ccc acc ctc cgc cac ctc ttc ctc tgc ctc tcc atg ctg<br>Leu Arg Cys Pro Thr Leu Arg His Leu Phe Leu Cys Leu Ser Met Leu<br>330                             335                         340                         345 | 1302 |
| tgg ttt gcc act agc ttt gca tac tat ggg ctg gtc atg gac ctg cag<br>Trp Phe Ala Thr Ser Phe Ala Tyr Tyr Gly Leu Val Met Asp Leu Gln<br>                   350                         355                         360 | 1350 |
| ggc ttt gga gtc agc atc tac cta atc cag gtg atc ttt ggt gct gtg<br>Gly Phe Gly Val Ser Ile Tyr Leu Ile Gln Val Ile Phe Gly Ala Val<br>                   365                         370                         375 | 1398 |
| gac ctg cct gcc aag ctt gtg ggc ttc ctt gtc atc aac tcc ctg ggt<br>Asp Leu Pro Ala Lys Leu Val Gly Phe Leu Val Ile Asn Ser Leu Gly<br>         380                         385                         390 | 1446 |
| cgc cgg cct gcc cag atg gct gca ctg ctg ctg gca ggc atc tgc atc<br>Arg Arg Pro Ala Gln Met Ala Ala Leu Leu Leu Ala Gly Ile Cys Ile<br>395                             400                         405 | 1494 |

-continued

| | | | | | | | | | | | | | | | |
|---|---|---|---|---|---|---|---|---|---|---|---|---|---|---|---|
| ctg | ctc | aat | ggg | gtg | ata | ccc | cag | gac | cag | tcc | att | gtc | cga | acc | tct | 1542 |
| Leu | Leu | Asn | Gly | Val | Ile | Pro | Gln | Asp | Gln | Ser | Ile | Val | Arg | Thr | Ser | |
| 410 | | | | 415 | | | | | 420 | | | | | 425 | | |

| | | | | | | | | | | | | | | | |
|---|---|---|---|---|---|---|---|---|---|---|---|---|---|---|---|
| ctt | gct | gtg | ctg | ggg | aag | ggt | tgt | ctg | gct | gcc | tcc | ttc | aac | tgc | atc | 1590 |
| Leu | Ala | Val | Leu | Gly | Lys | Gly | Cys | Leu | Ala | Ala | Ser | Phe | Asn | Cys | Ile | |
| | | | | | 430 | | | | | 435 | | | | | 440 | |

| | | | | | | | | | | | | | | | |
|---|---|---|---|---|---|---|---|---|---|---|---|---|---|---|---|
| ttc | ctg | tat | act | ggg | gaa | ctg | tat | ccc | aca | atg | atc | cgg | cag | aca | ggc | 1638 |
| Phe | Leu | Tyr | Thr | Gly | Glu | Leu | Tyr | Pro | Thr | Met | Ile | Arg | Gln | Thr | Gly | |
| | | | | 445 | | | | | 450 | | | | | 455 | | |

| | | | | | | | | | | | | | | | |
|---|---|---|---|---|---|---|---|---|---|---|---|---|---|---|---|
| atg | gga | atg | ggc | agc | acc | atg | gcc | cga | gtg | ggc | agc | atc | gtg | agc | cca | 1686 |
| Met | Gly | Met | Gly | Ser | Thr | Met | Ala | Arg | Val | Gly | Ser | Ile | Val | Ser | Pro | |
| | | | 460 | | | | | 465 | | | | | 470 | | | |

| | | | | | | | | | | | | | | | |
|---|---|---|---|---|---|---|---|---|---|---|---|---|---|---|---|
| ctg | gtg | agc | atg | act | gcc | gag | ctc | tac | ccc | tcc | atg | cct | ctc | ttc | atc | 1734 |
| Leu | Val | Ser | Met | Thr | Ala | Glu | Leu | Tyr | Pro | Ser | Met | Pro | Leu | Phe | Ile | |
| | 475 | | | | | 480 | | | | | 485 | | | | | |

| | | | | | | | | | | | | | | | |
|---|---|---|---|---|---|---|---|---|---|---|---|---|---|---|---|
| tac | ggt | gct | gtt | cct | gtg | gcc | gcc | agc | gct | gtc | act | gtc | ctc | ctg | cca | 1782 |
| Tyr | Gly | Ala | Val | Pro | Val | Ala | Ala | Ser | Ala | Val | Thr | Val | Leu | Leu | Pro | |
| 490 | | | | | 495 | | | | | 500 | | | | | 505 | |

| | | | | | | | | | | | | | | | |
|---|---|---|---|---|---|---|---|---|---|---|---|---|---|---|---|
| gag | acc | ctg | ggc | cag | cca | ctg | cca | gac | acg | gtg | cag | gac | ctg | gag | agc | 1830 |
| Glu | Thr | Leu | Gly | Gln | Pro | Leu | Pro | Asp | Thr | Val | Gln | Asp | Leu | Glu | Ser | |
| | | | | 510 | | | | | 515 | | | | | 520 | | |

| | | | | | | | | | | | | | | | |
|---|---|---|---|---|---|---|---|---|---|---|---|---|---|---|---|
| agg | tgg | gcc | ccc | act | cag | aaa | gaa | gca | ggg | ata | tat | ccc | agg | aaa | ggg | 1878 |
| Arg | Trp | Ala | Pro | Thr | Gln | Lys | Glu | Ala | Gly | Ile | Tyr | Pro | Arg | Lys | Gly | |
| | | | 525 | | | | | 530 | | | | | 535 | | | |

| | | | | | | | | | | | | | | | |
|---|---|---|---|---|---|---|---|---|---|---|---|---|---|---|---|
| aaa | cag | acg | cga | cag | caa | caa | gag | cac | cag | aag | tat | atg | gtc | cca | ctg | 1926 |
| Lys | Gln | Thr | Arg | Gln | Gln | Gln | Glu | His | Gln | Lys | Tyr | Met | Val | Pro | Leu | |
| | | | 540 | | | | | 545 | | | | | 550 | | | |

| | | | | | | | | | | |
|---|---|---|---|---|---|---|---|---|---|---|
| cag | gcc | tca | gca | caa | gag | aag | aat | gga | ctc | tgaggactga gaaggggcct | 1976 |
| Gln | Ala | Ser | Ala | Gln | Glu | Lys | Asn | Gly | Leu | |
| | 555 | | | | | 560 | | | | | tacagaaccc taagggagg gaaggtccta caggtctccg gccacccaca caaggaggag    2036 gaagaggaaa tggtgaccca agtgtgggg ttgtggttca ggaaagcatc ttcccagggg    2096 tccacctccc tttataaacc ccaccagaac cacatcatta aaggtttga ctgcgaaaaa    2156 aaaaaaaaaa aaaaa    2171

<210> SEQ ID NO 2
<211> LENGTH: 563
<212> TYPE: PRT
<213> ORGANISM: Rat

<400> SEQUENCE: 2

Met Ala Phe Asn Asp Leu Leu Gln Gln Val Gly Gly Val Gly Arg Phe
1               5                   10                  15

Gln Gln Ile Gln Val Thr Leu Val Leu Pro Leu Leu Leu Met Ala
            20                  25                  30

Ser His Asn Thr Leu Gln Asn Phe Thr Ala Ala Ile Pro Thr His His
        35                  40                  45

Cys Arg Pro Pro Ala Asp Ala Asn Leu Ser Lys Asn Gly Gly Leu Glu
    50                  55                  60

Val Trp Leu Pro Arg Asp Arg Gln Gly Gln Pro Glu Ser Cys Leu Arg
65                  70                  75                  80

Phe Thr Ser Pro Gln Trp Gly Leu Pro Phe Leu Asn Gly Thr Glu Ala
                85                  90                  95

Asn Gly Thr Gly Ala Thr Glu Pro Cys Thr Asp Gly Trp Ile Tyr Asp
            100                 105                 110

Asn Ser Thr Phe Pro Ser Thr Ile Val Thr Glu Trp Asp Leu Val Cys
        115                 120                 125

-continued

```
Ser His Arg Ala Leu Arg Gln Leu Ala Gln Ser Leu Tyr Met Val Gly
    130                 135                 140

Val Leu Leu Gly Ala Met Val Phe Gly Tyr Leu Ala Asp Arg Leu Gly
145                 150                 155                 160

Arg Arg Lys Val Leu Ile Leu Asn Tyr Leu Gln Thr Ala Val Ser Gly
                165                 170                 175

Thr Cys Ala Ala Phe Ala Pro Asn Phe Pro Ile Tyr Cys Ala Phe Arg
                180                 185                 190

Leu Leu Ser Gly Met Ala Leu Ala Gly Ile Ser Leu Asn Cys Met Thr
            195                 200                 205

Leu Asn Val Glu Trp Met Pro Ile His Thr Arg Ala Cys Val Gly Thr
    210                 215                 220

Leu Ile Gly Tyr Val Tyr Ser Leu Gly Gln Phe Leu Leu Ala Gly Val
225                 230                 235                 240

Ala Tyr Ala Val Pro His Trp Arg His Leu Gln Leu Leu Val Ser Ala
                245                 250                 255

Pro Phe Phe Ala Phe Phe Ile Tyr Ser Trp Phe Phe Ile Glu Ser Ala
                260                 265                 270

Arg Trp His Ser Ser Gly Arg Leu Asp Leu Thr Leu Arg Ala Leu
            275                 280                 285

Gln Arg Val Ala Arg Ile Asn Gly Lys Arg Glu Glu Gly Ala Lys Leu
    290                 295                 300

Ser Met Glu Val Leu Arg Ala Ser Leu Gln Lys Glu Leu Thr Met Gly
305                 310                 315                 320

Lys Gly Gln Ala Ser Ala Met Glu Leu Leu Arg Cys Pro Thr Leu Arg
                325                 330                 335

His Leu Phe Leu Cys Leu Ser Met Leu Trp Phe Ala Thr Ser Phe Ala
            340                 345                 350

Tyr Tyr Gly Leu Val Met Asp Leu Gln Gly Phe Gly Val Ser Ile Tyr
            355                 360                 365

Leu Ile Gln Val Ile Phe Gly Ala Val Asp Leu Pro Ala Lys Leu Val
    370                 375                 380

Gly Phe Leu Val Ile Asn Ser Leu Gly Arg Arg Pro Ala Gln Met Ala
385                 390                 395                 400

Ala Leu Leu Leu Ala Gly Ile Cys Ile Leu Leu Asn Gly Val Ile Pro
                405                 410                 415

Gln Asp Gln Ser Ile Val Arg Thr Ser Leu Ala Val Leu Gly Lys Gly
            420                 425                 430

Cys Leu Ala Ala Ser Phe Asn Cys Ile Phe Leu Tyr Thr Gly Glu Leu
            435                 440                 445

Tyr Pro Thr Met Ile Arg Gln Thr Gly Met Gly Met Gly Ser Thr Met
    450                 455                 460

Ala Arg Val Gly Ser Ile Val Ser Pro Leu Val Ser Met Thr Ala Glu
465                 470                 475                 480

Leu Tyr Pro Ser Met Pro Leu Phe Ile Tyr Gly Ala Val Pro Val Ala
                485                 490                 495

Ala Ser Ala Val Thr Val Leu Leu Pro Glu Thr Leu Gly Gln Pro Leu
            500                 505                 510

Pro Asp Thr Val Gln Asp Leu Glu Ser Arg Trp Ala Pro Thr Gln Lys
    515                 520                 525

Glu Ala Gly Ile Tyr Pro Arg Lys Gly Lys Gln Thr Arg Gln Gln Gln
530                 535                 540
```

```
Glu His Gln Lys Tyr Met Val Pro Leu Gln Ala Ser Ala Gln Glu Lys
545                 550                 555                 560

Asn Gly Leu

<210> SEQ ID NO 3
<211> LENGTH: 2171
<212> TYPE: DNA
<213> ORGANISM: Human
<220> FEATURE:
<221> NAME/KEY: CDS
<222> LOCATION: (268)...(1956)

<400> SEQUENCE: 3
gaaagctgag ctgccctgac ccccaaagtg aggagaagct gcaagggaaa agggagggac      60
agatcaggga gaccggggaa gaaggaggag cagccaagga ggctgctgtc ccccacaga     120 gcagctcgga ctcagctccc ggagcaaccc agctgcggag caacggcag tgctgctcct    180 ccagcgaagg acagcaggca ggcagacaga cagaggtcct gggactggaa ggcctcagcc   240
cccagccact gggctgggcc tggccca atg gcc ttt aat gac ctc ctg cag cag   294
                                Met Ala Phe Asn Asp Leu Leu Gln Gln
                                 1               5 gtg ggg ggt gtc ggc cgc ttc cag cag atc cag gtc acc ctg gtg gtc   342
Val Gly Gly Val Gly Arg Phe Gln Gln Ile Gln Val Thr Leu Val Val
 10              15                  20                  25 ctc ccc ctg ctc ctg atg gct tct cac aac acc ctg cag aac ttc act   390
Leu Pro Leu Leu Leu Met Ala Ser His Asn Thr Leu Gln Asn Phe Thr
         30                  35                  40 gct gcc atc cct acc cac cac tgc cgc ccg cct gcc gat gcc aac ctc   438
Ala Ala Ile Pro Thr His His Cys Arg Pro Pro Ala Asp Ala Asn Leu
     45                  50                  55 agc aag aac ggg ggg ctg gag gtc tgg ctg ccc cgg gac agg cag ggg   486
Ser Lys Asn Gly Gly Leu Glu Val Trp Leu Pro Arg Asp Arg Gln Gly
 60                  65                  70 cag cct gag tcc tgc ctc cgc ttc acc tcc ccg cag tgg gga ctg ccc   534
Gln Pro Glu Ser Cys Leu Arg Phe Thr Ser Pro Gln Trp Gly Leu Pro
 75                  80                  85 ttt ctc aat ggc aca gaa gcc aat ggc aca ggg gcc aca gag ccc tgc   582
Phe Leu Asn Gly Thr Glu Ala Asn Gly Thr Gly Ala Thr Glu Pro Cys
 90                  95                 100                 105 acc gat ggc tgg atc tat gac aac agc acc ttc cca tct acc atc gtg   630
Thr Asp Gly Trp Ile Tyr Asp Asn Ser Thr Phe Pro Ser Thr Ile Val
             110                 115                 120 act gag tgg gac ctt gtg tgc tct cac agg gcc cta cgc cag ctg gcc   678
Thr Glu Trp Asp Leu Val Cys Ser His Arg Ala Leu Arg Gln Leu Ala
         125                 130                 135 cag tcc ttg tac atg gtg ggg gtg ctc ctc gga gcc atg gtg ttc ggc   726
Gln Ser Leu Tyr Met Val Gly Val Leu Leu Gly Ala Met Val Phe Gly
     140                 145                 150 tac ctt gca gac agg cta ggc cgc cgg aag gta ctc atc ttg aac tac   774
Tyr Leu Ala Asp Arg Leu Gly Arg Arg Lys Val Leu Ile Leu Asn Tyr
 155                 160                 165 ctg cag aca gct gtg tca ggg acc tgc gca gcc ttc gca ccc aac ttc   822
Leu Gln Thr Ala Val Ser Gly Thr Cys Ala Ala Phe Ala Pro Asn Phe
170                 175                 180                 185 ccc atc tac tgc gcc ttc cgg ctc ctc tcg ggc atg gct ctg gct ggc   870
Pro Ile Tyr Cys Ala Phe Arg Leu Leu Ser Gly Met Ala Leu Ala Gly
             190                 195                 200 atc tcc ctc aac tgc atg aca ctg aat gtg gag tgg atg ccc att cac   918
Ile Ser Leu Asn Cys Met Thr Leu Asn Val Glu Trp Met Pro Ile His
         205                 210                 215
```

-continued

| | | |
|---|---|---|
| aca cgg gcc tgc gtg ggc acc ttg att ggc tat gtc tac agc ctg ggc<br>Thr Arg Ala Cys Val Gly Thr Leu Ile Gly Tyr Val Tyr Ser Leu Gly<br>220                          225                        230 | 966 |
| cag ttc ctc ctg gct ggt gtg gcc tac gct gtg ccc cac tgg cgc cac<br>Gln Phe Leu Leu Ala Gly Val Ala Tyr Ala Val Pro His Trp Arg His<br>    235                        240                        245 | 1014 |
| ctg cag cta ctg gtc tct gcg cct ttt ttt gcc ttc ttc atc tac tcc<br>Leu Gln Leu Leu Val Ser Ala Pro Phe Phe Ala Phe Phe Ile Tyr Ser<br>250                          255                        260                        265 | 1062 |
| tgg ttc ttc att gag tcg gcc cgc tgg cac tcc tcc ggg agg ctg<br>Trp Phe Phe Ile Glu Ser Ala Arg Trp His Ser Ser Ser Gly Arg Leu<br>            270                        275                        280 | 1110 |
| gac ctc acc ctg agg gcc ctg cag aga gtc gcc cgg atc aat ggg aag<br>Asp Leu Thr Leu Arg Ala Leu Gln Arg Val Ala Arg Ile Asn Gly Lys<br>    285                        290                        295 | 1158 |
| cgg gaa gaa gga gcc aaa ttg agt atg gag gta ctc cgg gcc agt ctg<br>Arg Glu Glu Gly Ala Lys Leu Ser Met Glu Val Leu Arg Ala Ser Leu<br>300                          305                        310 | 1206 |
| cag aag gag ctg acc atg ggc aaa ggc cag gca tcg gcc atg gag ctg<br>Gln Lys Glu Leu Thr Met Gly Lys Gly Gln Ala Ser Ala Met Glu Leu<br>    315                        320                        325 | 1254 |
| ctg cgc tgc ccc acc ctc cgc cac ctc ttc ctc tgc ctc tcc atg ctg<br>Leu Arg Cys Pro Thr Leu Arg His Leu Phe Leu Cys Leu Ser Met Leu<br>330                          335                        340                        345 | 1302 |
| tgg ttt gcc act agc ttt gca tac tat ggg ctg gtc atg gac ctg cag<br>Trp Phe Ala Thr Ser Phe Ala Tyr Tyr Gly Leu Val Met Asp Leu Gln<br>            350                        355                        360 | 1350 |
| ggc ttt gga gtc agc atc tac cta atc cag gtg atc ttt ggt gct gtg<br>Gly Phe Gly Val Ser Ile Tyr Leu Ile Gln Val Ile Phe Gly Ala Val<br>            365                        370                        375 | 1398 |
| gac ctg cct gcc aag ctt gtg ggc ttc ctt gtc atc aac tcc ctg ggt<br>Asp Leu Pro Ala Lys Leu Val Gly Phe Leu Val Ile Asn Ser Leu Gly<br>                380                        385                        390 | 1446 |
| cgc cgg cct gcc cag atg gct gca ctg ctg ctg gca ggc atc tgc atc<br>Arg Arg Pro Ala Gln Met Ala Ala Leu Leu Leu Ala Gly Ile Cys Ile<br>395                          400                        405 | 1494 |
| ctg ctc aat ggg gtg ata ccc cag gac cag tcc att gtc cga acc tct<br>Leu Leu Asn Gly Val Ile Pro Gln Asp Gln Ser Ile Val Arg Thr Ser<br>    410                        415                        420                        425 | 1542 |
| ctt gct gtg ctg ggg aag ggt tgt ctg gct gcc tcc ttc aac tgc atc<br>Leu Ala Val Leu Gly Lys Gly Cys Leu Ala Ala Ser Phe Asn Cys Ile<br>            430                        435                        440 | 1590 |
| ttc ctg tat act ggg gaa ctg tat ccc aca atg atc cgg cag aca ggc<br>Phe Leu Tyr Thr Gly Glu Leu Tyr Pro Thr Met Ile Arg Gln Thr Gly<br>                445                        450                        455 | 1638 |
| atg gga atg ggc agc acc atg gcc cga gtg ggc agc atc gtg agc cca<br>Met Gly Met Gly Ser Thr Met Ala Arg Val Gly Ser Ile Val Ser Pro<br>                460                        465                        470 | 1686 |
| ctg gtg agc atg act gcc gag ctc tac ccc tcc atg cct ctc ttc atc<br>Leu Val Ser Met Thr Ala Glu Leu Tyr Pro Ser Met Pro Leu Phe Ile<br>475                          480                        485 | 1734 |
| tac ggt gct gtt cct gtg gcc gcc agc gct gtc act gtc ctc ctg cca<br>Tyr Gly Ala Val Pro Val Ala Ala Ser Ala Val Thr Val Leu Leu Pro<br>490                          495                        500                        505 | 1782 |
| gag acc ctg ggc cag cca ctg cca gac acg gtg cag gac ctg gag agc<br>Glu Thr Leu Gly Gln Pro Leu Pro Asp Thr Val Gln Asp Leu Glu Ser<br>                        510                        515                        520 | 1830 |
| agg tgg gcc ccc act cag aaa gaa gca ggg ata tat ccc agg aaa ggg<br>Arg Trp Ala Pro Thr Gln Lys Glu Ala Gly Ile Tyr Pro Arg Lys Gly<br>            525                        530                        535 | 1878 |

```
aaa cag acg cga cag caa caa gag cac cag aag tat atg gtc cca ctg    1926
Lys Gln Thr Arg Gln Gln Gln Glu His Gln Lys Tyr Met Val Pro Leu
            540                 545                 550 cag gcc tca gca caa gag aag aat gga ctc tgaggactga aagggcct        1976
Gln Ala Ser Ala Gln Glu Lys Asn Gly Leu
            555                 560 tacagaaccc taaagggagg gaaggtccta caggtctccg gccacccaca caaggaggag  2036
gaagaggaaa tggtgaccca agtgtggggg ttgtggttca ggaaagcatc ttcccagggg  2096
tccacctccc tttataaacc ccaccagaac cacatcatta aaggtttga ctgcgaaaaa   2156 aaaaaaaaaa aaaaa                                                   2171

<210> SEQ ID NO 4
<211> LENGTH: 563
<212> TYPE: PRT
<213> ORGANISM: Human

<400> SEQUENCE: 4

Met Ala Phe Asn Asp Leu Leu Gln Gln Val Gly Gly Val Gly Arg Phe
  1               5                  10                  15

Gln Gln Ile Gln Val Thr Leu Val Val Leu Pro Leu Leu Leu Met Ala
             20                  25                  30

Ser His Asn Thr Leu Gln Asn Phe Thr Ala Ala Ile Pro Thr His His
         35                  40                  45

Cys Arg Pro Pro Ala Asp Ala Asn Leu Ser Lys Asn Gly Gly Leu Glu
     50                  55                  60

Val Trp Leu Pro Arg Asp Arg Gln Gly Gln Pro Glu Ser Cys Leu Arg
 65                  70                  75                  80

Phe Thr Ser Pro Gln Trp Gly Leu Pro Phe Leu Asn Gly Thr Glu Ala
                 85                  90                  95

Asn Gly Thr Gly Ala Thr Glu Pro Cys Thr Asp Gly Trp Ile Tyr Asp
            100                 105                 110

Asn Ser Thr Phe Pro Ser Thr Ile Val Thr Glu Trp Asp Leu Val Cys
        115                 120                 125

Ser His Arg Ala Leu Arg Gln Leu Ala Gln Ser Leu Tyr Met Val Gly
    130                 135                 140

Val Leu Leu Gly Ala Met Val Phe Gly Tyr Leu Ala Asp Arg Leu Gly
145                 150                 155                 160

Arg Arg Lys Val Leu Ile Leu Asn Tyr Leu Gln Thr Ala Val Ser Gly
                165                 170                 175

Thr Cys Ala Ala Phe Ala Pro Asn Phe Pro Ile Tyr Cys Ala Phe Arg
            180                 185                 190

Leu Leu Ser Gly Met Ala Leu Ala Gly Ile Ser Leu Asn Cys Met Thr
        195                 200                 205

Leu Asn Val Glu Trp Met Pro Ile His Thr Arg Ala Cys Val Gly Thr
    210                 215                 220

Leu Ile Gly Tyr Val Tyr Ser Leu Gly Gln Phe Leu Leu Ala Gly Val
225                 230                 235                 240

Ala Tyr Ala Val Pro His Trp Arg His Leu Gln Leu Leu Val Ser Ala
                245                 250                 255

Pro Phe Phe Ala Phe Phe Ile Tyr Ser Trp Phe Phe Ile Glu Ser Ala
            260                 265                 270

Arg Trp His Ser Ser Gly Arg Leu Asp Leu Thr Leu Arg Ala Leu
        275                 280                 285
```

-continued

```
Gln Arg Val Ala Arg Ile Asn Gly Lys Arg Glu Glu Gly Ala Lys Leu
        290                 295                 300

Ser Met Glu Val Leu Arg Ala Ser Leu Gln Lys Glu Leu Thr Met Gly
305                 310                 315                 320

Lys Gly Gln Ala Ser Ala Met Glu Leu Leu Arg Cys Pro Thr Leu Arg
                325                 330                 335

His Leu Phe Leu Cys Leu Ser Met Leu Trp Phe Ala Thr Ser Phe Ala
            340                 345                 350

Tyr Tyr Gly Leu Val Met Asp Leu Gln Gly Phe Gly Val Ser Ile Tyr
        355                 360                 365

Leu Ile Gln Val Ile Phe Gly Ala Val Asp Leu Pro Ala Lys Leu Val
    370                 375                 380

Gly Phe Leu Val Ile Asn Ser Leu Gly Arg Arg Pro Ala Gln Met Ala
385                 390                 395                 400

Ala Leu Leu Leu Ala Gly Ile Cys Ile Leu Leu Asn Gly Val Ile Pro
                405                 410                 415

Gln Asp Gln Ser Ile Val Arg Thr Ser Leu Ala Val Leu Gly Lys Gly
            420                 425                 430

Cys Leu Ala Ala Ser Phe Asn Cys Ile Phe Leu Tyr Thr Gly Glu Leu
        435                 440                 445

Tyr Pro Thr Met Ile Arg Gln Thr Gly Met Gly Met Gly Ser Thr Met
    450                 455                 460

Ala Arg Val Gly Ser Ile Val Ser Pro Leu Val Ser Met Thr Ala Glu
465                 470                 475                 480

Leu Tyr Pro Ser Met Pro Leu Phe Ile Tyr Gly Ala Val Pro Val Ala
                485                 490                 495

Ala Ser Ala Val Thr Val Leu Leu Pro Glu Thr Leu Gly Gln Pro Leu
            500                 505                 510

Pro Asp Thr Val Gln Asp Leu Glu Ser Arg Trp Ala Pro Thr Gln Lys
        515                 520                 525

Glu Ala Gly Ile Tyr Pro Arg Lys Gly Lys Gln Thr Arg Gln Gln Gln
    530                 535                 540

Glu His Gln Lys Tyr Met Val Pro Leu Gln Ala Ser Ala Gln Glu Lys
545                 550                 555                 560

Asn Gly Leu
```

METHOD FOR SCREENING USING AN OAT1 TRANSPORTER PROTEIN

TECHNICAL FIELD

The present invention is related to the genes and their encoding polypeptides, which are related to the transport of organic anions.

BACKGROUND ART

The kidney plays important roles in the excretion of endogenous compounds and xenobiotics. Anionic substances including drugs are excreted via carrier-mediated pathway(s) into the urine. The first step of this secretion is the uptake of organic anion from the peritubular plasma across the basolateral membrane of the proximal tubule cells.

The basolateral uptake of the organic anions has been studied using several techniques, such as perfusion of excised kidney, or membrane vesicles of isolated tubule cells. In these studies, para-aminohippurate (PAH) has been widely used as a test substrate. During these studies, it has been supposed that the organic anion transporter responsible for the basolateral uptake of organic anions was an organic anion/dicarboxylate exchanger.

There are, however, limitations in the previous techniques for precise analysis of the organic anions transport, such as the networks of transport between different transporters and the drug—drug interaction against a single molecule. Thus, the isolation of the organic anion transporter molecule which enables more precise analysis of the organic anion transporter has been eagerly awaited.

So far, several transporter molecules which are expressed in the liver have been isolated (Hagenbuch, B. et al. Proc. Natl. Acad. Sci. U.S.A. 88, 10629–10633, 1991, Jacquemin, E. et al. Proc. Natl. Acad. Sci. U.S.A. 91, 133–137, 1994). The cDNA cloning of organic cation transporter (OCT1), which is expressed in the kidney and the liver, was also reported (Grundemann, D. et al. Nature 372, 549–52, 1994).

As a sodium-dependent dicarboxylate cotransporter, the cDNA encoding sodium-dicarboxylate co-transporter (NaDC-1) was reported (Pajor, A. M. J. Biol. Chem. 270, 5779–5785, 1995).

Recently, OAT-K1, an isoform of oatp was isolated (Saito, H. et al. J. Biol. Chem. 271, 20719–20725, 1996). Oatp is organic anion transporting polypeptide which is expressed in the liver and mediates the sodium-independent transport of organic anions. OAT-K1 is expressed in the renal proximal tubules, however, the transport properties of OAT-K1 was distinct from that of the organic anion/dicarboxylate exchanger of the renal proximal tubule cells.

DISCLOSURE OF THE INVENTION

The aim of the present invention is to provide novel genes and the gene products, which are related to the renal transport of organic anions. The other aims of this invention will be explained in the following.

BRIEF EXPLANATIONS OF THE FIGURES

BEST MODE FOR CARRYING OUT THE INVENTION

Figure 1:
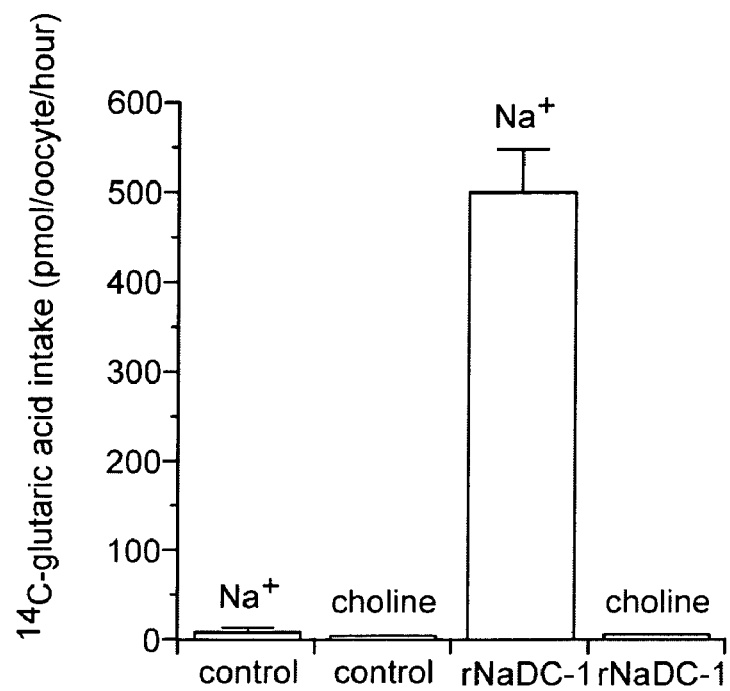
FIG. 1 shows the uptake of glutarate by the oocytes injected with rat sodium dependent dicarboxylate cotransporter (rNaDC-1) cRNA.

We isolated a novel cDNA which encodes a membrane protein, OAT1, from the rat kidney. We also isolated the human homolog of OAT1. We expressed rat and human OAT1 in the *Xenopus laevis* oocytes, and successfully demonstrated that these proteins mediated the transport of organic anions. Thus we could complete this invention.

(A) The protein whose amino acid sequence is shown in SEQ ID NO: 1.

(B) The proteins whose amino acid sequences are identical to that shown in SEQ ID NO: 1 except that several amino acid residues are deleted, substituted or added in it. Despite of these changes, the protein must possess the ability to transport organic anions. Despite of these changes, the protein must possess the ability to transport organic anions.

(C) The protein whose amino acid sequence is shown in SEQ ID NO: 2.

(D) The proteins whose amino acid sequences are identical to that shown in SEQ ID NO: 2 except that several amino acid residues are deleted, substituted or added in it. Despite of these changes, the protein must possess the ability to transport organic anions.

The DNAs whose nucleotide sequences are described in a, b, c and d are also includes in this invention.

(a) The DNA whose nucleotide sequence is shown in SEQ ID NO: 1.

(b) DNAs which can hybridize the DNA shown in SEQ ID NO: 1 in stringent condition, and encode the proteins possessing the ability to transport organic anions.

(c) The DNA whose nucleotide sequence is shown in SEQ ID NO: 2.

(d) DNAs which can hybridize the DNA shown in SEQ ID NO: 2 in stringent condition, and encode the proteins possessing the ability to transport organic anions.

The novel protein of the present invention (OAT1: organic anion transporter 1) which possesses the ability to transport organic anions, is expressed predominantly in the renal proximal tubule cells.

The transport rate of organic anions via OAT1, i.e. the uptake rate of organic anions into the cell expressing OAT1, is stimulated by dicarboxylates present in the cells. This fact indicates that OAT1 is an organic anion/dicarboxylate exchanger. The dicarboxylates which are effluxed in exchange for organic anion via OAT1, are taken up by the sodium-dicarboxylate cotransporter from the extracellular fluid. Thus, dicarboxylate are recycled for the OAT1-mediated transport of organic anions.

The novel protein of the present invention, OAT1, possesses the ability to transport (take up) various organic anions, such as cycic nucleotides, prostaglandins, urate, antibiotics, diuretics and anticancer drugs. Since chemical structures of these substances are diverse, the substrate selectivity of OAT1 is considered to be very wide.

The amino acid sequence of OAT1 shows no similarity to that of the previously isolated renal organic anions transporter OAT-K1. Thus, OAT1 belongs to distinct transporter family.

The SEQ ID NO: 1 shown in the table depicts the total nucleotide sequence of rat OAT1 cDNA (approximately 2.2 kb) with the deduced amino acid sequence (551 amino acid residue) encoded by the open reading frame of rat OAT1 cDNA.

The SEQ ID NO: 2 shown in the table depicts the total nucleotide sequence of human OAT1 cDNA (approximately 2.2 kb) with the deduced amino acid seqence (563 amino acid residue) encoded by the open reading frame of human cDNA.

We searched for the DNA database (GeneBank and EMBL) and protein database (NBRF and SWISS-PROT) for the homologues sequence of OAT1. We could not find any homologues sequences of OAT1 in the sequences whose function had been clarified.

In addition to the amino acid sequence shown in SEQ ID NO: 1 and SEQ ID NO: 2, the present invention includes the following proteins. Proteins whose amino acid sequences are identical to that shown in SEQ ID NO: 1 except that several amino acid sequence of these proteins are acceptable when the product proteins possess the ability to transport organic anions. Usually, numbers of the changed amino acid residues are between one to 110, preferably 1 to 55. These amino acid sequences show 80% or more, preferably 90°% or more homology to SEQ ID NO: 1 or SEQ ID NO: 2.

In addition to the DNAs with the nucleotide sequences shown in SEQ ID NO: 1 and SEQ ID NO: 2, the present invention includes DNAs which can hybridize the cDNA shown in SEQ ID NO: 1 and SEQ ID NO: 2. The proteins encode by these DNAs must possess the ability to transport organic anions. Usually, these DNAs show more than 70%, preferably 80% or more homology to SEQ ID NO: 1 or SEQ ID NO: 2. These DNAs include mutated genes found in nature, artificially modified genes and the genes derived from other species of living cells.

The stringent condition in hybridization screening, which we refer to in this invention, indicates that hybridization is performed at 37–42° C. for approximately 12 hours in 5×SSC (Standard Saline Citrate) solution, or in the hybridization solution with equivalent concentrations of salts, followed by washing in 1×SSC solution. If more high stringency condition is required, washing process can be performed in 0.1×SSC or solutions with equivalent concentrations of salts.

The homologues genes encoding the organic anion transporter of the present invention, can be obtained from other species, such as the dogs, bovines, horses, gouts, sheep, monkeys, pigs, rabbits and mouse, using homology screening. For this purpose, cDNA library can be constructed from the kidney or culture cells of the aimed species of animals.

In addition to the homology screening, the isolation of the genes can be performed using expression cloning technique.

In the following, we will explain the method of expression cloning briefly, which we used for the isolation of the renal organic anion transporter.

mRNA (poly $(A)^+$ RNA) obtained from the rat kidney is divided into fractions according to their size, and each fraction of mRNA is injected into *Xenopus laevis* oocytes with cRNA of rat sodium-dependent dicarboxylate cotransporter.

The cDNA sequence of rabbit sodium dicarboxylate cotransporter (NaDC-1) was already reported (Pajor, A. M. J. Biol. Chem. 270, 5779–5785, 1995), therefore, the cDNA of rat sodium dicarboxylate cotransporter (NaDC-1) can be easily isolated. The complementary RNA (cRNA) for rNaDC-1 cDNA can be synthesized in vitro using RNA polymerases, such as T3 or T7 RNA polymerase.

Oocytes injected with rat kidney mRNA and the cRNA of rNaDC-1 are examined for the uptake rate of radio-labeled organic anions, such as PAH, and the mRNA fractions showing the highest transport rate of PAH can be determined. The cDNA library can be constructed from these selected fractions, which should contain concentrated mRNA for the PAH transporter. cRNAs can be synthesizes from the constructed cDNAs and injected into oocytes with the rNaDC-1 cRNA. By repeating the screening, the cDNA which encodes the PAH transporter can be isolated.

The sequence of the obtained clone can be determined by dideoxytermination method, and the deduced amino acid sequence encoded can be predicted.

Whether the cDNA obtained really encodes the organic anion transporter can be verified as follows. cRNA synthesized from the isolated cDNA clone is injected into *Xenopus* oocytes, and ability of the expressed protein to transport of organic anions can be examined as described elsewhere (Kanai, Y. and Hediger, M. A. (1992) Nature 360, 467–471).

Functional analysis of the organic anion transporter, such as the exchange property of OAT1, can be examined using the oocytes expressing OAT1.

Using the cDNA of rat OAT1, homologues DNAs or chromosomal genes derived from different tissues or different animals can be obtained from appropriate cDNA or genomic library.

Based on the sequence of this invention shown in SEQ ID NO: 1 and SEQ ID NO: 2, sets of PCR (polymerase chain reaction) primers can be designed by which cDNA probes can be synthesized to search the cDNA or genomic library.

cDNA library or genomic DNA library can be constructed using methods described, for example, in "Molecular Cloning" edited by Sambrook, J., Fritsch, E. F., and Maniatis, T. Cold Spring Harbor Laboratory Press, 1989. Commercially available library can also be used.

The organic anion transporter of this invention can be produced by the molecular recombination technique. For example, the cDNA encoding the organic anion transporter is subcloned into expression vectors, followed by transformation p f appropriate host cells with them. For expression systems to produce polypeptides, host cells, such as bacteria, yeast, insect and mammalian cells can be used. Among these, insects cells and mammalian cells are preferable to obtain the proteins with functions.

When the organic anion transporter is required to be expressed in the mammalian cells, the cDNA encoding the organic anion transporter should be subcloned into mammalian expression vectors, such as retrovirus vectors, papilloma virus vectors, vaccinia virus vectors and SV40 vectors. In this case, the cDNA of organic anion transporter must be inserted after? the promoter regions, such as SV40 promoter, LTR promoter and elongation 1α promoter. Then appropriate animal cells are transformed with the recombinant vectors containing the organic anion transporter cDNA. The mammalian cells, such as COS7 cells, CHO cells, Hela cells, primary culture cells derived from the kidney, LLC-PK1 cells and OK cells, can be used for this purpose.

The cDNAs which can be used for the above mentioned purpose are not restricted to those shown in SEQ ID NO: 1 and SEQ ID NO: 2. Since each amino acid is encoded by several types of codon, cDNAs which encode the proteins with the amino acid sequences shown in SEQ ID NO: 1 and SEQ ID NO: 2 can be designed based on information of codons. Any codon, which encode the desired amino acid, can be selected, and cDNAs inducing more efficient expression may be designed considering the codon preference in the host cells. The designed cDNAs can be obtained by chemical DNA synthesis, digestion and ligation technique, and site-directed mutagenesis method. The methods of the site directed mutagenesis are described elsewhere (Mark, D. F., et al., Pro Nat Aca Sci, vol 81, 5662–5666, 1984).

The nucleotides which can hybridize the cDNA of OAT1 in high stringent condition can be used as probes to detect the organic anion transporters. In addition, they can be used to alter the expression level of the organic anion transporter, such as antisense-nucleotide, ribozyme and decoy. For this purpose, continuous nucleotides more than 14 base pairs, or their complementary nucleotide sequences can be used. If more specificity is required, more longer fragments, for example more than 20 to 30 nucleotides sequence, can be applied.

The antibody against the organic anion transporter of this invention can be obtained, using the fragments of the organic anion transporter or the synthesized polypeptides with the partial sequences which have equivalent immunochemical properties. Polyclonal antibody can be obtained by the ordinary immunizing method. i.e. immunize the rat or rabbit with antigen, and recover the serum. Monoclonal antibody can be obtained by the ordinary method such as hybridoma technique. These antibody can be used to detect or purify the organic anion transporter.

In the following, we will explain the present invention precisely, however, this invention is not restricted to the following description.

This invention has been performed, if not indicated otherwise, using methods described in the "Molecular Cloning" (edited by Sambrook, J., Fritsch, E. F., and Maniatis, T., Cold Spring Harbor Laboratory Press, 1989), or using commercially available reagents and kits according to the manufacturer instructions.

EXAMPLES

Example 1

Cloning of Rat Organic Anion Transporter (1) cDNA Cloning of Rat Sodium-dicarboxylate Co-Transporter (rNaDC-1), and the Preparation of rNaDC-1 cRNA A non-directional cDNA library was prepared from rat kidney poly(A)+ RNA using commercially available kit (Superscript Choice system, GIBCO BRL) and was ligated to λZipLox EcoRI arms (GIBCO BRL). A PCR product corresponding to nucleotides 1323 1763 of the rabbit sodium dicarboxylate transporter (NaDC-1) (Pajor, A. M. (1995) J. Biol. Chem. 270, 5779–5785) was labeled with $^{32}$P-dCTP. A rat cDNA library was screened with this probe at low stringency. Hybridization was done overnight in the hybridization solution at 37° C. and filters were washed finally at 37° C. in 0.1×SSC/0.1% SDS. The hybridization solution contains 5×SSC, 3× Denhardt's solution, 0.2% SDS, 10% dextran sulfate, 50% formamide, 0.01% Antifoam B, 0.2 mg/ml denatured salmon sperm DNA, 2.5 mM sodium pyrophosphate and 25 mM MES, pH 6.5. cDNA inserts in positive λZipLox phage were recovered in plasmid pZL1 by in vivo excision and further subcloned into pBluescript II SK– (Stratagene) for sequencing and in vitro transcription.

rNaDC-1 cRNA was synthesized in vitro using the rNaDC-1 cDNA as a template.

*Xenopus laevis* oocyte expression studies and uptake measurements were performed as described elsewhere (Kanai, Y. and Hediger, M. A. (1992) Nature 360, 467–471, 1992). Defolliculated oocytes were injected with in vitro transcribed cRNA of rNaDC-1, and $^{14}$C-glutarate uptake was examined in ND96 solution (96 mM NaCl, 2 mM KCl, 1.8 mM CaCl2, 1 mM MgCl2, 5 mM HEPES, pH 7.4).

As shown in FIG. 1, the oocytes injected with rNaDC-1 cRNA showed the sodium-dependent uptake of glutarate, indicating that the isolated rNaDC-1 encodes the rat sodium-dependent dicarboxylate cotransporter.

(2) Cloning of the Rat Renal Organic Anion Transporter OAT1.

The expression cloning of organic anion transporter 1 (OAT1) was performed using the method described elsewhere (Kanai, Y. and Hediger, M. A. (1992) Nature 360, 467–471, 1992).

Four hundreds µg of rat kidney poly(A)+ RNA was size fractionated as described elsewhere (Kanai, Y. and Hediger, M. A. (1992) Nature 360, 467–471, 1992) using preparative gel electrophoresis (BIO RAD, Model 491 Prep cell).

Then we co-injected poly(A)$^+$ RNAs of each fraction together with rNaDC-1 cRNA into oocytes. Before uptake study, the oocytes were routinely preincubated for two hours in ND96 solution containing 1 mM glutarate for 2 hours.

Figure 2:
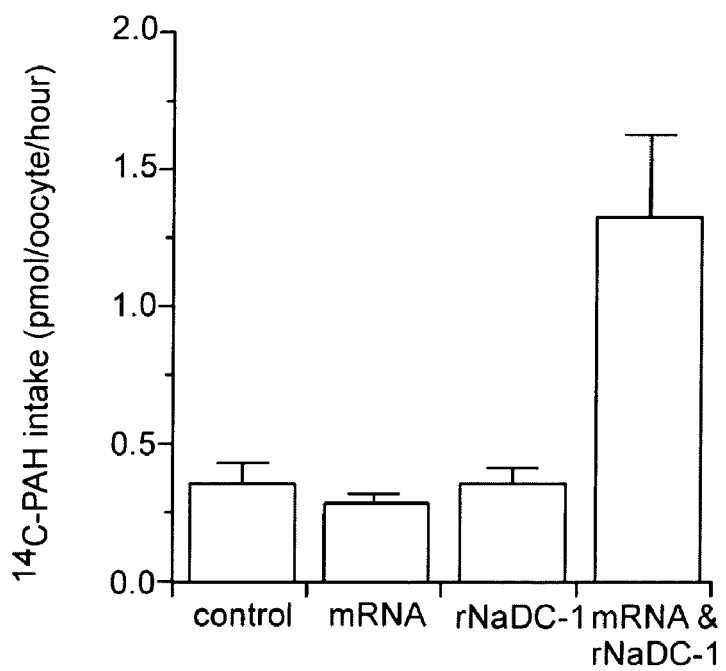
FIG. 2 shows the uptake experiment using the oocytes injected with rat kidney mRNA and/or rNaDC-1 cRNA.

Uptake experiment was performed in oocytes injected with poly(A)+ RNAs of each fraction together with rNaDC-1 cRNA. $^{14}$C-PAH (50 µM) uptake was measured in ND96 solution without glutarate for 1 hour. In this experiment, only those oocytes injected with both poly(A)$^+$ RNAs of each fraction and rNaDC-1 cRNA showed significant uptake of PAH: in contrast oocytes injected with only poly(A)$^+$ RNAs of each fraction or rNaDC-1 cRNA did not show any uptake of PAH (FIG. 2).

We determined the cRNA fractions (1.8–2.4 kilobase (kb) poly (A)$^+$ RNA), which induced the highest PAH uptake rate when injected with rNaDC-1 cRNA into X oocytes. Then a directional cDNA library was constructed from these fractions using Superscript Plasmid system (GIBCO BRL), and was ligated into the Sal I and Not I site of pSPORT 1. Recombinants were electroporated into Electro Max DH10B competent cells (GIBCO BRL). Approximately 500 colonies were grown on nitrocellulose membrane. Plasmid DNA was purified from colonies of each plate. Capped cRNA was synthesized in vitro after linearization of each plasmid DNA with Not I.

Then we co-injected cRNA synthesized from each filter together with 2 ng rNaDC-1 cRNA into oocytes. When $^{14}$C-PAH uptake was detected on a particular group, it was subdivided into several groups, and further screened.

After screening of eight thousands clones, we isolated a single clone (OAT1), which mediated the significant uptake of PAH.

Deleted clones obtained by Kilo-Sequence Deletion kit (Takara, Japan) or specially synthesized oligonucleotide primers were used for sequencing of OAT1 cDNA. OAT1 were sequenced by dideoxytermination method using Sequenase ver. 2.0 (Amersham) or Dye Primer Cycle Sequencing Kit (Applied Biosystems).

Then we determined the nucleotide sequence of OAT1, and deduced the coding region of OAT1 cDNA and the amino acid sequence encoded.

The nucleotide SEQ ID NO: 1 is the sequence of OAT 1.

Figure 3:
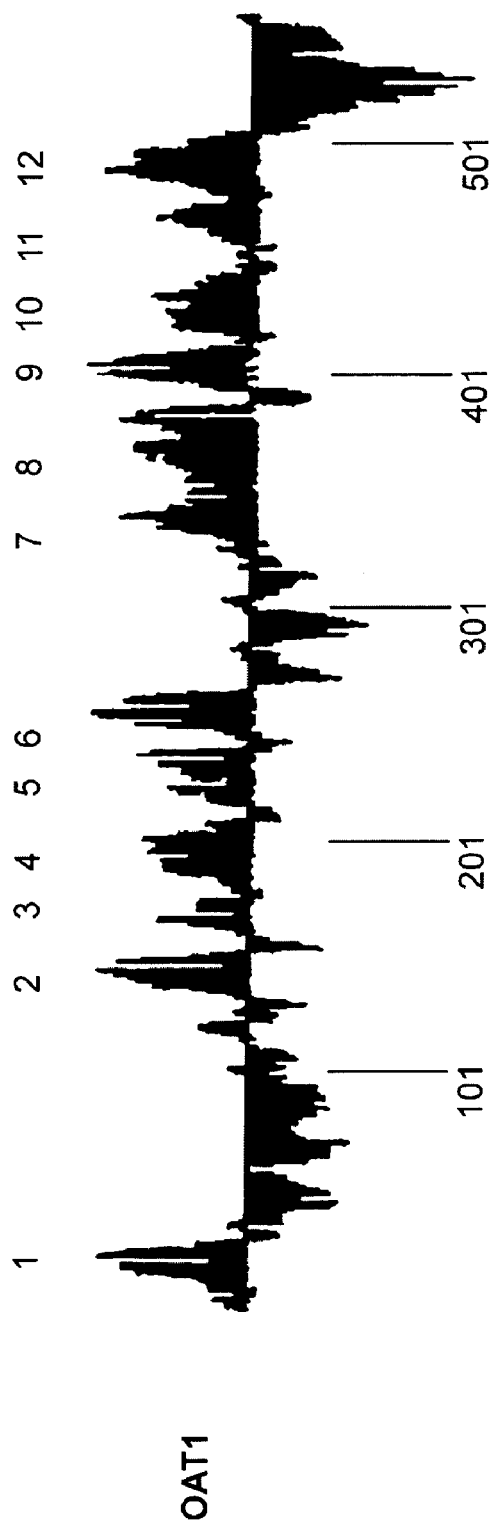
FIG. 3 shows Hydropathy analysis of rat organic anion transporter OAT1.

Kyte-Doolittle hydropathy analysis (Kyte, J. and Doolittle, R. F. (1982) J. Mol. Biol. 157, 105–132) of OAT1 predicts twelve putative membrane-spanning domains (FIG. 3). Five N-glycosylation sites are predicted in the first hydrophilic loop. There are 4 putative protein kinase C-dependent phosphorylation sites in the hydrophilic loop between 6 th and 7 th transmembrane domains.

(3) The Tissue Distribution of OAT1 Analyzed by Northern Blot

The tissue distribution of OAT1 mRNA was examined. Three $\mu$g of poly (A)+ RNA prepared from various rat tissues were electrophoresed on a 1% agarose/formaldehyde gel and transferred to a nitrocellulose filter. The filter was hybridized at 42° C. overnight in the hybridization solution with full-length OAT1 cDNA labeled with $^{32}$P-dCTP. The filter was washed finally in 0.1×SSC/0.1% SDS at 65° C.

Figure 4:
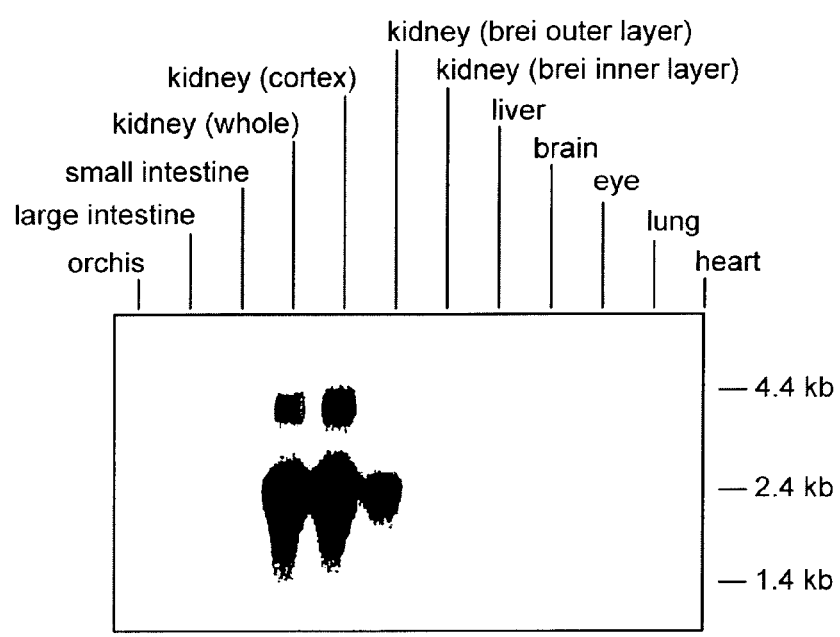
FIG. 4 shows Northern blot analysis of rat organic anion transporter OAT1 using mRNAs derived form various rat tissues.

Under high stringency Northern blot analysis, a strong 2.4 kb mRNA band and two bands corresponding to longer transcripts (3.9 kb and 4.2 kb) were detected predominantly in the kidney (FIG. 4). In the kidney, expression of OAT1 mRNA is strong in the cortex and outer medulla (cortex>outer medulla) and very weak in the inner medulla.

Upon longer exposure, a faint 2.4 kb mRNA band was detected in the brain. No hybridization signals were obtained with mRNA isolated from other tissues.

(4) Intrarenal Expression of OAT1 mRNA Analyzed by in situ Hybridization

The intrarenal expression of OAT1 was examined by in situ hybridization analysis. In situ hybridization was performed as described elsewhere (Kanai, Y. and Hediger, M. A. (1992) Nature 360, 467–471, 1992) with some modifications. Briefly, after perfusion fixation with 4% paraformaldehyde, rat kidney was excised and postfixed in 4% paraformaldehyde. Five $\mu$m cryostat sections of rat kidney were used in situ hybridization.

$^{35}$S-labeled sense and antisense cRNA were synthesized from the full-length OAT1 cDNA (in pBlueScript SK−) using T7 or T3 RNA polymerase after linearization of plasmid DNA with Spe I or Xho I, respectively. The cryosections were hybridized with the probe overnight in the hybridization solution, and washed to a final stringency of 0.1×SSC at 37° C. for 30 min.

In situ hybridization of rat kidney coronal sections revealed that OAT1 mRNA is expressed in renal cortex and outer medulla, especially in the medullary rays of the cortex. Expression of OAT1 was not found in the inner medulla. This overall pattern of in situ hybridization suggests that OAT1 is most strongly expressed in the middle portion of the proximal tubule (S2).

Example 2

Functional Characterization of Organic Anion Transporter 1 (OAT1)

(1) The Effect of the Preincubation of Glutarate on the Transport Activity of OAT1

The effect of the preincubation of glutarate was investigated in the uptake experiment using the oocytes expressed with OAT1.

The uptake experiment using PAH was performed as described in the methods of EXAMPLE 1-(2). Oocytes injected with rat OAT1 cRNA only, or both rat OAT1 and rNaDC-1 cRNA were incubated in the ND96 solution containing $^{14}$C-PAH for 1 hour after preincubated them in the ND96 solution with and without 1 mM of glutarate.

Figure 5:
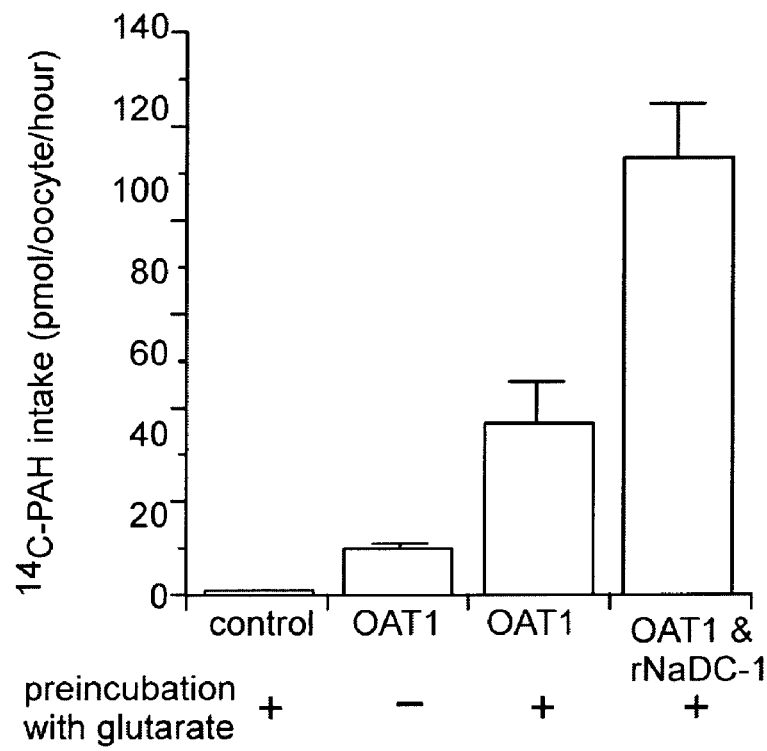
FIG. 5 shows the effect of pre-incubation with glutarate, or co-expression with rNaDC-1 was examined in oocytes injected with rat OAT1.

FIG. 5 shows the dependence of OAT1-mediated $^{14}$C-PAH uptake on the intracellular dicarboxylate (glutarate) concentration. The rate of $^{14}$C-PAH uptake by oocytes via OAT1 is increased by preincubation of the oocytes with 1 mM glutarate. When oocytes co-expressing rNaDC-1 and OAT1 are preincubated with glutarate, hey showed a further increase in the rate of $^{14}$C-PAH uptake. This trans-stimulative effect of glutarate indicates that OAT1 is an organic anion/dicarboxylate exchanger. Control oocytes are those which were not injected with cRNA.

(2) The Sodium Dependency of the Transport Activity of OAT1

The effect of the extracellular sodium ion on the OAT1-mediated uptake of PAH was examined.

The uptake experiment using PAH was performed as described in the methods of EXAMPLE 2-(1). In this experiment, choline 96 solution, in which 96 mM sodium chloride was replaced with equimolar of choline chloride, was also used in addition to ND96 solution.

Figure 6:
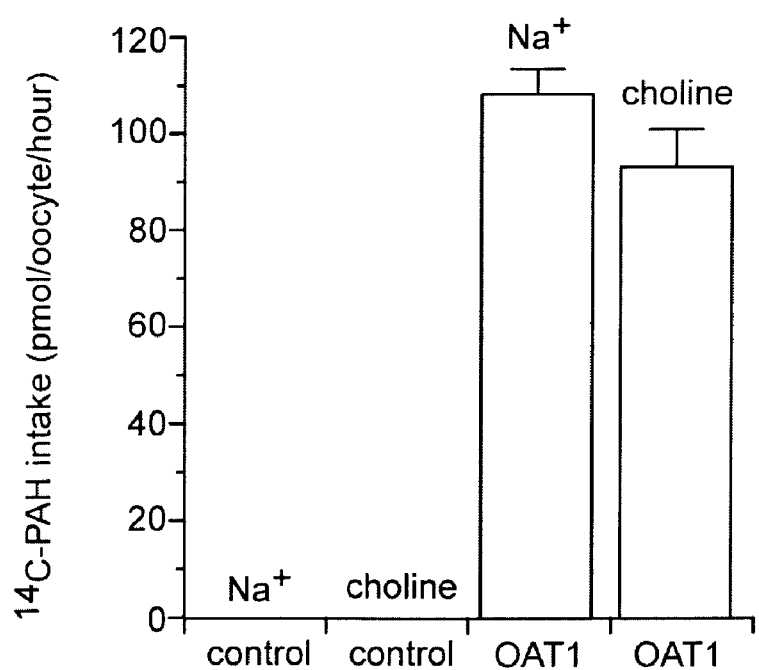
FIG. 6 shows the effect of extracellular sodium ion on the rat OAT1-mediated uptake of PAH in oocytes injected with OAT1 cRNA.

As shown in FIG. 6, replacement of extracellular sodium with choline had no effect on the rate of $^{14}$C-PAH uptake, indicating that OAT1 is a sodium independent transporter. Control oocytes were those which were not injected with cRNA.

(3) The Kinetic Experiment

Transport rate of different concentrations of PAH via OAT1 was measured to obtain the kinetic parameters of OAT1.

Figure 7:
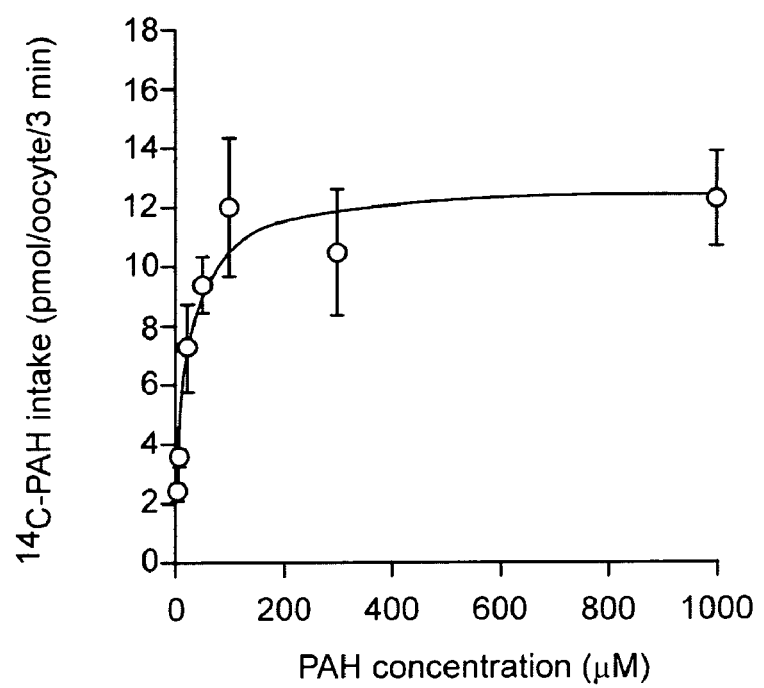
FIG. 7 shows transport rate of different concentrations of PAH in oocytes injected with rat OAT1 cRNA was examined.

The uptake experiment using PAH was performed as described in the methods of EXAMPLE 2-(1). $^{14}$C-PAH uptake was measured for 3 minutes. As shown in FIG. 7, OAT1-mediated PAH uptake followed Michaelis-Menten kinetics, and the estimated Km value was 14.3±2.9 $\mu$M (mean±s.e.m., N=3). This values is similar to that previously reported for the basolateral organic anion transport system (80 $\mu$M) (Ullrich, K. J. and Rumrich, G. Am. J. Physiol. 254, F453–462, 1988).

(4) The Substrate Selectivity of OAT1 Examined by Inhibition Study

The effect of various anionic drugs on the PAH uptake in the oocytes injected with rat OAT1 cRNA.

The uptake experiment using PAH was performed as described in the methods of EXAMPLE 2-(1). In this experiment, 2 $\mu$M of $^{14}$C-PAH uptake in oocytes injected with rat OAT1 cRNA was measured in the ND96 solution with and without 2 mM of various non-labeled substances.

Figure 8:
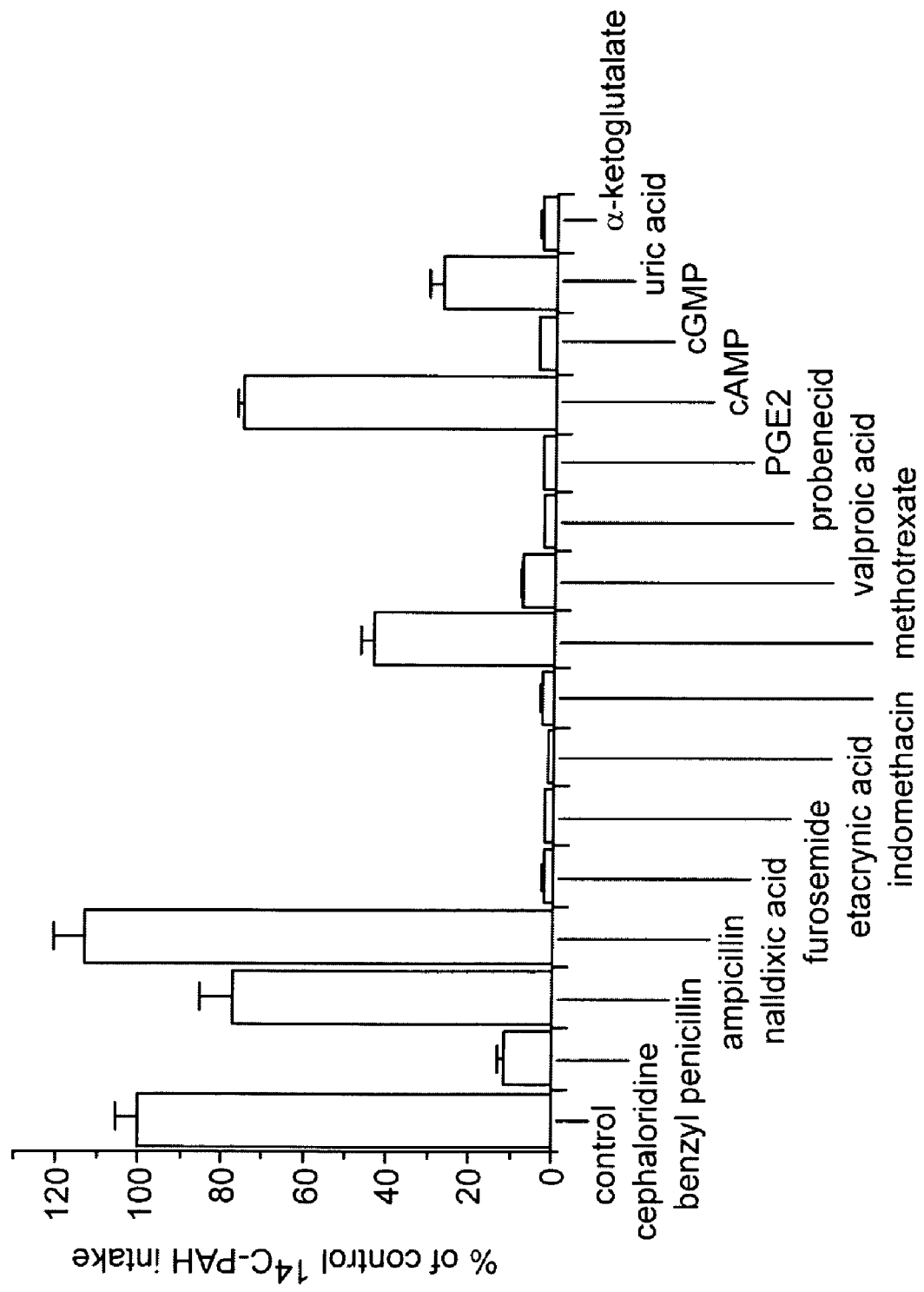
FIG. 8 shows Cis-inhibitory effect of various anionic substances on the rat OAT1-mediated uptake of PAH was examined.

As shown in FIG. 8, cis-Inhibitory effect was observed for structurally unrelated drugs. Cephaloridine (a β-lactam antibiotic), nalidixic acid (an "old" quinolone), furosemide and ethacrynic acid (diuretics), indomethacin (a nonsteroidal anti-inflammatory drug), probenecid (an uricosuric drug) and valproic acid (an antiepileptic drug) potently inhibited (>85%) OAT1-mediated $^{14}$C-PAH uptake. An antineoplastic drug, methotrexate, moderately inhibited $^{14}$C-PAH uptake. Endogenous compounds, such as prostaglandin E2, cyclic-AMP, cyclic-GMP and uric acid also inhibited $^{14}$C-PAH uptake.

(5) The Substrate Selectivity of OAT1 Examined by Uptake Experiment Using Labeled Anionic Substances Several radio labeled compounds were examined whether they are taken up into oocytes via OAT1.

The uptake experiment using PAH was performed as described in the methods of EXAMPLE 2-(1). In this experiment, radio labeled substances were used as substrates in stead of $^{14}$C-PAH. Control oocytes were those which were not injected with cRNA.

Figure 9:
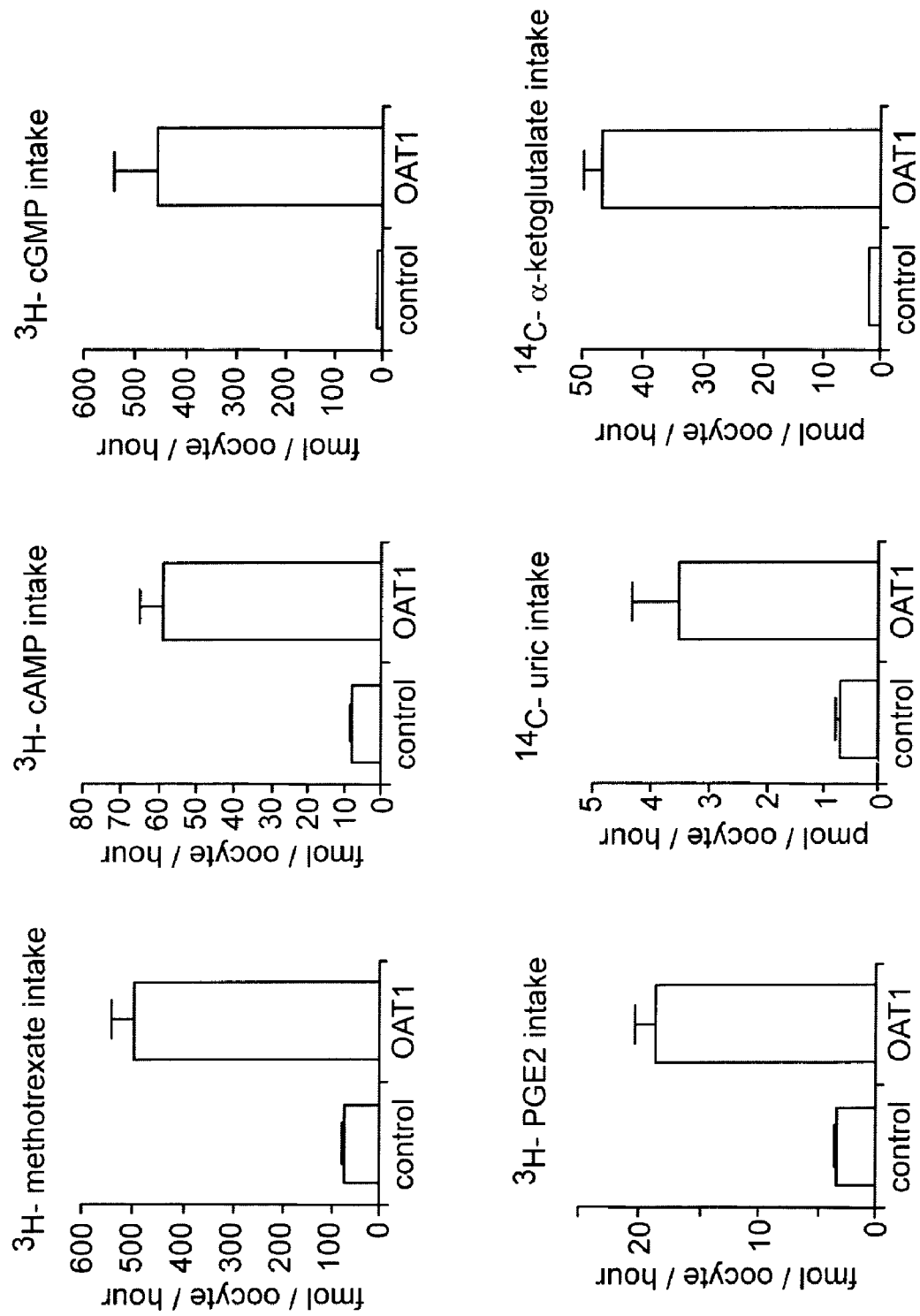
FIG. 9 shows the result of that radio labeled drugs was examined whether they were transported by rat OAT1.

As shown in FIG. 9, $^3$H-methotrexate, $^3$H-cAMP, $^3$H-cGMP, $^3$H-prostaglandin E2, $^{14}$C-urate and $^{14}$C-α-ketoglutarate were revealed to be transported into the oocytes expressing OAT1. In contrast, any uptake of $^{14}$C-TEA (tetraethylammonium: a representative organic cation) and $^3$H-taurocholic acid were not detected (data not shown).

Example 3

Cloning of the Human Organic Anion Transporter

Using rat OAT1 cDNA obtained in EXAMPLE 1-(2), human cDNA library was screened. Human cDNA library was constructed from human kidney poly (A)+ RNA (Clontech).

Sequence of the isolated cDNA clone (human OAT1 cDNA) was determined according to the methods described in Example 1. The coding region of the human OAT1 cDNA and the deduce amino acid sequence was determined as well.

The sequence of human OAT1 in both nucleotide and amino acid level is shown in SEQ ID NO: 2.

The sequence homology between rat OAT1 and human OAT1 was approximately 85% and 79%, in amino acid level and nucleotide level, respectively.

INDUSTRIAL APPLICABILITY

The present invention, organic anion transporter 1 (OAT1) and the gene encoding OAT1, is considered to be useful to clarify the molecular mechanisms underlying the pharmacokinetics and toxicokinetics, such as the drug elimination and drug—drug interaction. In addition, the screening system to identify the nephrotoxic drugs and the way to protect kidney from such nephrotoxic substances will be developed, since many agents causing renal insufficiency, such as β-lactam antibiotics and NSAIDs (non-steroidal anti inflammatory drugs), have been suggested to be transported by OAT1, and OAT1 seems to be responsible for the accumulation of these nephrotoxicants in the kidney.

The invention claimed is:

1. Method for screening a compound for an effect on the ability of a protein to transport an organic anion, wherein the method comprises the steps of:
   cultivating, in the presence of a substrate comprising said organic anion, an oocyte expressing the protein comprising the amino acid sequence of SEQ ID NO: 2;
   measuring the amount of organic anion transported into the oocyte; and
   comparing the amount of organic anion transported in the absence of said compound to the amount of organic anion transported in the presence of said compound.

2. The method of claim 1, wherein the protein comprising SEQ ID NO 2 is encoded by a nucleic acid isolated from a human.

3. The method of claim 1, wherein the protein comprising: the amino acid sequence of SEQ ID NO 2 is encoded by a nucleic acid isolated from kidneys.

4. A method for screening a compound inhibiting uptake of an organic anion into an oocyte, wherein the method comprises the steps of:
   (a) cultivating a first oocyte expressing a protein comprising the amino acid sequence of SEQ ID NO 2, wherein the cultivation is conducted in the presence of a labeled organic anion and a test compound;
   (b) cultivating a second oocyte expressing a protein comprising the amino acid sequence of SEQ ID NO 2, wherein the cultivation is conducted in the presence of a labeled organic anion;
   (c) measuring the amount of labeled organic anion transported into the first oocyte in step (a) and the amount of labeled organic anion transported into the second oocyte in step (b); and
   (d) comparing the amount of labeled organic anion transported as measured in step (a).

5. A method for screening an organic anion for an effect on the ability of a protein to transport an organic anion, wherein the method comprises the steps of:

cultivating an oocyte, in the presence of a substrate comprising said organic anion;

measuring the amount of organic anion transported into the oocyte; and comparing the amount of organic anion transported when the oocyte is expressing the protein comprising the amino acid sequence of SEQ ID NO 2, to the amount of organic anion transported in the absence of said protein.

6. The method of claim 5, wherein the protein comprising SEQ ID NO 2 is encoded by a nucleic acid isolated from a human.

7. The method of claim 5, wherein the protein comprising the amino acid sequence of SEQ ID NO 2 is encoded by a nucleic acid isolated from kidneys.

* * * * *